United States Patent
Diehl

(10) Patent No.: US 10,040,811 B2
(45) Date of Patent: Aug. 7, 2018

(54) MULTI-ELEMENT STANDARD FOR NUCLEAR MAGNETIC RESONANCE SPECTROSCOPY

(71) Applicant: Merck Patent GmbH, Darmstadt (DE)

(72) Inventor: Bernd Willi Karl-Heinz Diehl, Cologne (DE)

(73) Assignee: Merck Patent GmbH, Darmstadt (DE)

( * ) Notice: Subject to any disclaimer, the term of this patent is extended or adjusted under 35 U.S.C. 154(b) by 597 days.

(21) Appl. No.: 14/387,520

(22) PCT Filed: Mar. 15, 2013

(86) PCT No.: PCT/EP2013/055371
§ 371 (c)(1),
(2) Date: Sep. 23, 2014

(87) PCT Pub. No.: WO2013/139698
PCT Pub. Date: Sep. 26, 2013

(65) Prior Publication Data
US 2015/0077104 A1 Mar. 19, 2015

(30) Foreign Application Priority Data
Mar. 23, 2012 (DE) ........................ 10 2012 204 701

(51) Int. Cl.
| | | |
|---|---|---|
| C07F 9/36 | (2006.01) | |
| C07F 9/09 | (2006.01) | |
| C07F 9/12 | (2006.01) | |
| C07F 9/32 | (2006.01) | |
| G01N 24/08 | (2006.01) | |
| G01R 33/58 | (2006.01) | |
| G01R 33/46 | (2006.01) | |

(52) U.S. Cl.
CPC ............... *C07F 9/36* (2013.01); *C07F 9/094* (2013.01); *C07F 9/12* (2013.01); *C07F 9/3282* (2013.01); *G01N 24/087* (2013.01); *G01R 33/58* (2013.01); *G01R 33/4633* (2013.01)

(58) Field of Classification Search
CPC ........................................................ C07F 9/36
See application file for complete search history.

(56) References Cited

PUBLICATIONS

Database CA [online] Chemical Abstracts Service, Columbus, Ohio US; Klumpp, Egon et al. "Production of new phosphoric acid ester insecticides", Database accession No. 1990:118978.
Database CA [online] Chemical Abstracts Service, Columbus, Ohio US; Metcalf, Robert A et al. "Selective toxicity of analogs of methyl parathion", Database accession No. 1973:488307.
Database CA [online] Chemical Abstracts Service, Columbus, Ohio US; Maniara, Grzegorz et al. "Method performance and validation for quantitative analysis by 1H and 31P agricultural chemicals", Database accession No. 1998:697364.

*Primary Examiner* — Golam M Shameem
(74) *Attorney, Agent, or Firm* — Lewis Kohn & Walker LLP; David M. Kohn; Kari Moyer-Henry

(57) ABSTRACT

Organic compounds which contain nitrogen, fluorine, and phosphorus atoms together with carbon atoms and hydrogen atoms and which can be used as a multi-element standard for $^1$H—, $^{13}$C—, $^{15}$N—, $^{19}$F—, and $^{31}$P nuclear magnetic resonance spectroscopy. Also, a nuclear magnetic resonance spectroscopy method, preferably a quantitative nuclear magnetic resonance spectroscopy method, using said compounds and a method for qualitatively and/or quantitatively determining an analyte using such a nuclear magnetic resonance spectroscopy method.

13 Claims, 2 Drawing Sheets

MULTI-ELEMENT STANDARD FOR NUCLEAR MAGNETIC RESONANCE SPECTROSCOPY

Figure 1:
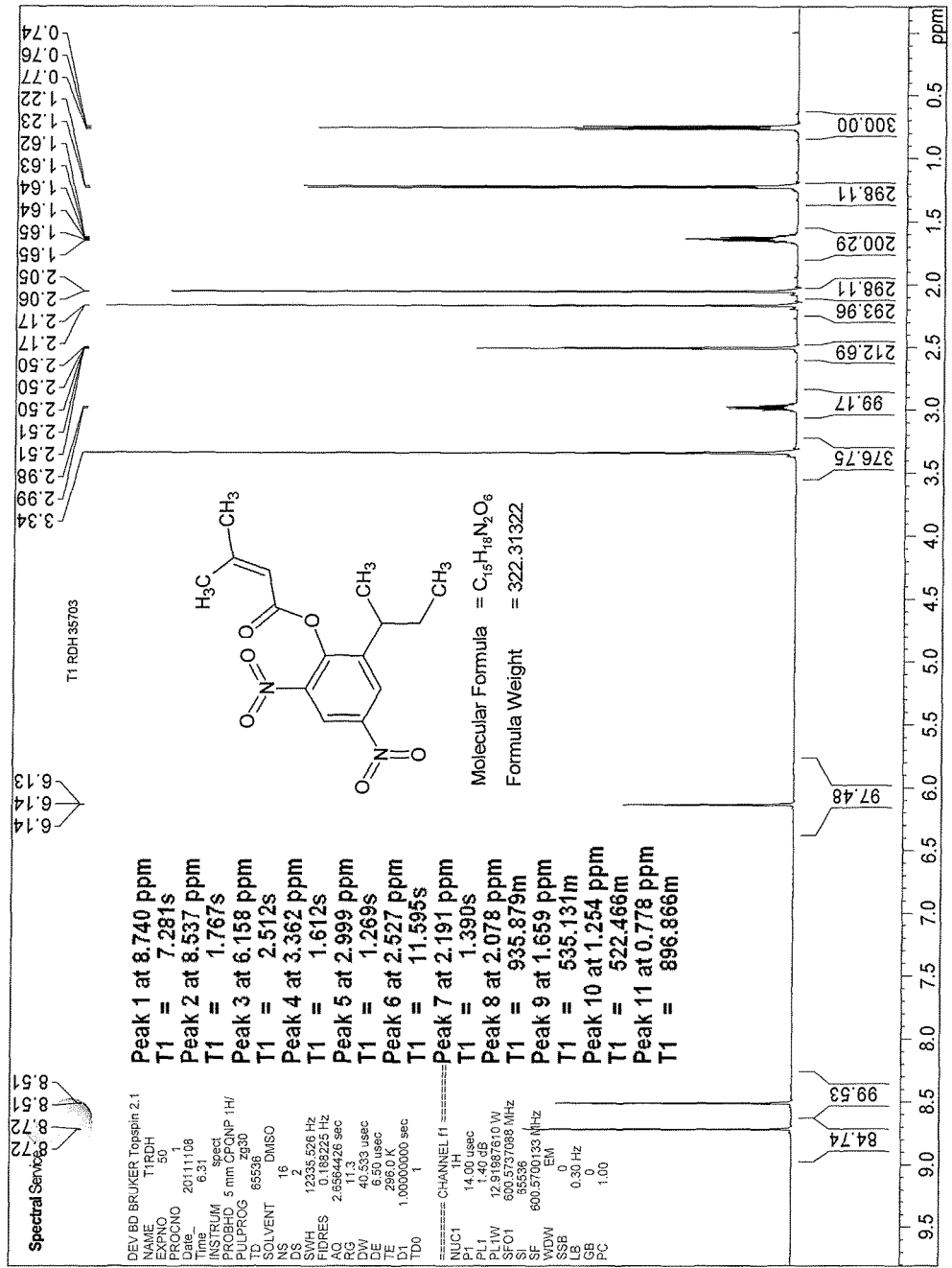

This application is a United States National Stage Application claiming the benefit of priority under 35 U.S.C. 371 from International Patent Application No. PCT/EP2013/055371 filed Mar. 15, 2013, which claims the benefit of priority from German Patent Application Serial No. DE 10 2012 204 701.8 filed Mar. 23, 2012, the entire contents of which are herein incorporated by reference.

DESCRIPTION

The present invention relates to organic compounds which as well as carbon atoms and hydrogen atoms also contain nitrogen, fluorine, and phosphorus atoms and can be used as a multinuclear standard for $^1$H, $^{13}$C, $^{15}$N, $^{19}$F and $^{31}$P nuclear magnetic resonance spectroscopy, and to an NMR standard which comprises these compounds. The present invention relates, furthermore, to a nuclear magnetic resonance spectroscopy method using these compounds, and to a method for determining an analyte by means of a nuclear magnetic resonance spectroscopy method of this kind.

Nuclear magnetic resonance spectroscopy, also called NMR spectroscopy hereinafter, is one of the fundamental methods for the structural resolution of organic compounds. The basis for the technique is that the atomic nuclei of a multiplicity of elements exhibit a nonzero nuclear spin, and the resultant angular momentum in an applied external magnetic field furnishes information about the chemical environment of the atom.

Atoms having a nuclear spin of zero, such as $^2$D, $^{12}$C, or $^{16}$O, for example, cannot be detected by means of NMR spectroscopy. Conversely, all atoms with a nonzero nuclear spin are accessible to NMR spectroscopy. Most advantageously, the nuclear spin has a value of ½, since in that case there are only two possible eigenstates, m=+½ and m=−½. In the application of NMR spectroscopy in organic chemistry, therefore, the nuclei in question are primarily $^1$H, $^{13}$C, $^{15}$N, $^{19}$F, $^{29}$Si, $^{31}$P, and $^{77}$Se.

When a sample which includes atomic nuclei having a nonzero nuclear spin is brought into a homogeneous, static magnetic field, quantum theory dictates that the angular momentum of the atomic nuclei is able to occupy only predetermined orientations with respect to the applied magnetic field. The possible orientations represent different eigenstates, which are split up energetically, forming quantized energy levels. If then, in addition to the applied static magnetic field, a high-frequency alternating electromagnetic field is generated, and if its energy corresponds to the energy difference of two eigenstates, then a part of the energy of the alternating field is absorbed by the sample—this can be captured by measuring technology and displayed graphically. What is being captured in this case specifically is the frequency of the high-frequency alternating electromagnetic field at which the resonance condition of the atomic nucleus is fulfilled—i.e., the nuclear resonance frequency.

The nuclear resonance frequencies determined provide information about the structure of the organic compound under analysis, through the chemical shift effect. This effect describes the influence of adjacent atoms or groups on the electron shell which surrounds the atomic nucleus under analysis, and which shields it from the external magnetic field. The quantized energy levels of the eigenstates are dependent on the strength of the external magnetic field acting on the atomic nucleus, and hence also on the extent of the shielding provided by its electron shell.

Looking, for example, at a hydrogen atom, different nuclear resonance frequencies arise according to whether in the vicinity of said atom there is an electron-withdrawing atom or an atom that increases electron density, or a corresponding group. Furthermore, anisotropic effects and steric effects also influence the chemical shift. Accordingly, for the different hydrogen atoms in an organic compound, different nuclear resonance frequencies are obtained, and can be displayed graphically as signals in a spectrum, with their evaluation having the capacity to provide valuable information for structural resolution. Additional information is obtained through spin-spin couplings of adjacent atomic nuclei, whereby the signals displayed in the spectrum are split up into groups of two or more signals. Such spin-spin couplings may occur between nuclei both of the same and of different elements.

Factors affecting the position of the nuclear resonance frequencies, in addition to the chemical environment of the atom, include the strength of the static magnetic field and the solvent used, and the position cannot therefore be compared on the basis of an absolute scale. In order nevertheless to allow comparison of NMR spectra with one another, the position of the nuclear resonance frequencies is reported in relation to a reference compound. In $^1$H and $^{13}$C NMR spectroscopy, tetramethylsilane (TMS) has long been used for this purpose. Owing to the symmetry of the molecule, all 12 hydrogen nuclei have the same resonance frequency, which, furthermore, lies at the upfield edge of the spectrum because of the electropositive character of silicon (strong shielding effect). The position of a resonance frequency of a hydrogen atom in the sample is reported in a $^1$H NMR spectrum as a relative shift of this frequency relative to the nuclear resonance frequency of the hydrogen atoms in TMS, and referred to as chemical shift δ. In view of the small frequency differences, this dimensionless value is reported in ppm ($=10^{-6}$).

In order to achieve the conditions for resonance, it is possible either to vary the frequency of the irradiated alternating field, with a constant field strength of the external magnetic field, or to vary the field strength with a constant frequency. These modes of scanning of the spectra are referred to under the heading of continuous wave methods (CW methods). Nowadays, however, it is predominantly pulse-Fourier transform technology (PFT NMR spectroscopy) that is employed, in which a high-frequency pulse is irradiated onto the sample, the frequency band of said pulse simultaneously exciting all of the nuclei of one nuclear type. The subsequent fall in magnetization, the free induction decay (FID), is measured and a spectrum is calculated from it by means of Fourier transformation. Through the summation of a multiplicity of FIDs, this technique can be used to analyze significantly smaller sample quantities.

During FID, the excited atomic nuclei go back into their equilibrium state—that is, they relax. A distinction is made here between two relaxation processes: longitudinal relaxation, or spin-lattice relaxation, and transverse relaxation, or spin-spin relaxation. The rate of longitudinal relaxation is characterized by the longitudinal relaxation time $T_1$. So that the system has largely achieved its equilibrium state again between two excitation pulses, it is customary to observe a waiting time of $5T_1$. If not all of the nuclei had relaxed before the next pulse, not all of the nuclei would be captured in that pulse, and false signal intensities would result. The length of the longitudinal relaxation time $T_1$ is dependent on the chemical structure of the molecule, more particularly on possible dipole-dipole interactions with adjacent atoms or groups, and can be up to more than 10 s.

In addition to pure structural resolution, NMR spectroscopy can also be employed for the quantitative determination of a compound under analysis, i.e., an analyte. In quantitative NMR spectroscopy, the amount of analyte present in the solution under analysis is calculated from a comparison of the signal intensities of the analyte and of a reference substance which undergoes measurement at the same time. In general, the reference substance added to the solution under analysis is an internal standard, which has a known purity and has signals which as far as possible are not superimposed on those of the analyte. The reference substance may also be used as an external standard. In the text below, a reference substance used in NMR spectroscopy is also referred to as a "standard". This standard may be used as an internal standard, being added to the solution under analysis, or else may be used as an external standard.

In the measured NMR spectrum, the signals of the analyte and of the reference substance are integrated separately. An assumption made here is that every atom whose signals appear in the spectrum contributes an equal proportion to the integrals of the signals, meaning that the number of atoms is proportional to the integrals, i.e., to the integral areas. From the ratio of the integrals, and taking account of the masses and molar masses of analyte and reference substance and the number of nuclei whose signals have been integrated, it is possible to calculate the molar amount of the analyte present in the solution under analysis.

In principle any organic compound of which at least one signal can be evaluated quantitatively in the NMR spectrum can be used as a reference substance. In order to allow the preparation of solutions of known concentration, the compound ought, furthermore, to be easy to weigh out, in other words not hygroscopic or volatile, and it ought preferably to be in the form of a solid. It should be chemically stable and should generate very few signals in the spectrum, preferably appearing separately from those of the analyte. To allow the concentration of the standard to be verified easily, it would be advantageous for the reference substance to be a good chromophore in UV/VIS and/or to be readily detectable by gas chromatography. Since it is used generally as an internal standard, it ought also, of course, to be readily soluble in the usual NMR solvents.

Many of the reference substances commonly used for quantitative NMR spectroscopy that generate a singlet signal in the $^1$H NMR spectrum, such as maleic acid and tetrachloronitrobenzene (TCNB)

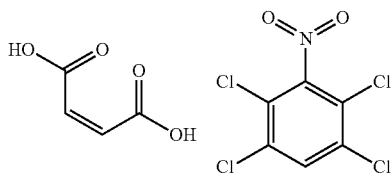 [SMILES: O=C(O)/C=C\C(=O)O ; O=[N+]([O-])c1c(Cl)c(Cl)cc(Cl)c1Cl]

for example, have long spin-lattice relaxation times. In the case of TCNB, $T_1$ is greater than 10 s.

So that the reference substance used is not limiting in the analysis of small amounts of sample and in the consequently necessary summation of a large number of FIDs, the substance ought preferably to have a short spin-lattice relaxation time. This time ought preferably to be 5 s or below.

As mentioned in the introduction, in NMR spectroscopy, alongside $^1$H and $^{13}$C, the nuclei $^{15}$N, $^{19}$F, and $^{31}$P are also utilized. The reference substances known to date and used in particular in quantitative NMR spectroscopy are suitable only for the spectroscopic contemplation of one or at most two types of nucleus. If another type of nucleus is to be measured as well in the same sample, this has to date required the addition of other standards, a costly and inconvenient procedure especially in quantitative NMR spectroscopy, since it requires that precisely defined standard solutions be prepared and precisely metered. These further standard solutions, furthermore, must also be monitored regularly for their purity, which constitutes an additional cost and complexity.

It is an object of the present invention, therefore, to provide reference substances with which in $^1$H, $^{13}$C, $^{15}$N, $^{19}$F, and $^{31}$P NMR spectroscopy, especially quantitative NMR spectroscopy, the above-described advantages can be avoided without detriment to the accuracy of the method. With these reference substances, moreover, it is also to be possible to analyze even small amounts of a very wide variety of analytes, without running the risk of differences in spin-lattice relaxation times falsifying the results. It is an object of the present invention, furthermore, to provide a quantitative nuclear magnetic resonance spectroscopy method for these nuclei and to provide a method for quantitative determination of an analyte by means of a nuclear magnetic resonance spectroscopy method of this kind.

In relation to the provision of suitable reference substances, the above object is achieved in accordance with the present invention as follows:

A) The compounds of the formula (1) or (2)

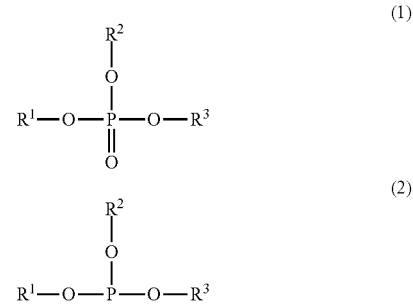

where $R^1$ is a phenyl radical or benzyl radical whose benzene ring has the following substituents:
at least one —$CF_3$ substituent,
at least one nitrogen-containing substituent selected from —$NO_2$ and —$NR^4R^5$, where $R^4$ and $R^5$ independently of one another are selected from H, $CH_3$, and $CH_2CH_3$,
optionally one or two substituents selected from Cl, Br, I, —$CH_3$, and —C(=O)$OR^6$, where $R^6$ is selected from H, $CH_3$, and $CH_2CH_3$, and
at least one hydrogen atom, where at least one of the hydrogen atoms is ortho to at least one substituent selected from —$NO_2$ and —C(=O)$OR^6$, and
where $R^2$ and $R^3$ are the same as $R^1$ or independently of one another are selected from H, $CH_3$, and $CH_2CH_3$, B) the use of a compound of the above formula (1) or (2) as a standard in $^1$H, $^{13}$C, $^{15}$N, $^{19}$F or $^{31}$P nuclear magnetic resonance spectroscopy, and C) an NMR standard which comprises a compound of the formula (1) or (2) above.

The present invention further provides a nuclear magnetic resonance spectroscopy method wherein the nuclear spin resonance of one of the atoms $^1$H, $^{13}$C, $^{15}$N, $^{19}$F, or $^{31}$P is detected, characterized in that a compound of the formula (1) or (2) above is used as standard.

Lastly, the present invention provides a method for qualitative and/or quantitative determination of an analyte by means of $^1$H, $^{13}$C, $^{15}$N, $^{19}$F, or $^{31}$P nuclear magnetic resonance spectroscopy, characterized in that a compound of the formula (1) or (2) above is used as standard.

The compounds of the formula (1) and (2) are phosphoric and phosphonic esters, respectively, and in addition to carbon atoms and hydrogen atoms they also contain nitrogen, fluorine, and phosphorus atoms, and can therefore be used as multinuclear standards for $^1$H, $^{13}$C, $^{15}$N, $^{19}$F, or $^{31}$P nuclear magnetic resonance spectroscopy. As a result there is no need for the preparation, holding, and monitoring of a plurality of standards or standard solutions, or for the addition of a plurality of standards to one sample when more than one type of nucleus in that sample is to be analyzed by NMR spectroscopy.

The compounds of the invention are used preferably as an internal standard.

The use of one of the compounds of the invention as a standard in NMR spectroscopy means that the compound is added to and dissolved in the solution under analysis, which comprises the compound under analysis (the analyte), and the solution under analysis, following addition of the standard, is then measured in an NMR spectrometer.

By virtue of the fact that the compounds of the formula (1) and (2) include nitrogen-, fluorine-, and phosphorus-containing groups, they are accessible for a series of quantification methods with which the purity of the standard can be simply determined or verified.

In the compounds of the formulae (1) and (2), at least one of the hydrogen atoms on the benzene ring is ortho to at least one substituent selected from —$NO_2$ and —$C(=O)OR^6$. Because of the influence of these adjacent and strongly electron-withdrawing groups, the signal of this hydrogen atom appears downfield in a $^1$H NMR spectrum, preferably at $\delta \geq 8$. The probability of this signal overlapping with signals of the analyte is therefore small. Preferably there is no other hydrogen atom in ortho-position to this hydrogen atom. As a result, spin-spin coupling is prevented, and the aromatic hydrogen atom is represented as a singlet in the spectrum.

If the electron-withdrawing group ortho to the hydrogen atom is the group —$C(=O)OR^6$, then $R^6$ is selected from H, $CH_3$, and $CH_2CH_3$, in order to produce few additional signals in the spectrum. Preferably $R^6$ is H or $CH_3$.

Of the two electron-withdrawing groups —$NO_2$ and —$C(=O)OR^6$, the $NO_2$ group is preferred, since it does not generate any additional signals in the spectrum.

In the multinuclear standard compound of the invention, the nitrogen atom may be present in the form of an $NO_2$ group or amino group, with the nitrogen atom in that case being bonded directly to the benzene ring. In the case of an amino group bonded to the benzene ring, the two radicals $R^4$ and $R^5$ are independently of one another H, $CH_3$, or $CH_2CH_3$, with H and $CH_3$ being preferred.

Of the two possible nitrogen-containing groups, the $NO_2$ group bonded directly to the benzene ring is preferred, since consequently, on the one hand, no additional signals are generated in $^1$H or $^{13}$C NMR spectra, and on the other hand a hydrogen atom positioned ortho to the $NO_2$ group appears in a $^1$H NMR spectrum at a high chemical shift.

The $\delta$ values for the chemical shift as stated in the present application are defined in relation to the chemical shift of the hydrogen atoms or carbon atoms of tetramethylsilane, which are fixed at 0 ppm in each case.

The substituted benzene ring in the compound of the formula (1) or (2) may be bonded directly in the form of a phenyl radical or via a methylene group ($CH_2$ group) in the form of a benzyl radical to the oxygen atom of the phosphoric or phosphonic acid group. Attachment by the methylene group produces a dipole-dipole interaction with the phosphorus atom, thereby reducing its relaxation time $T_1$ and hence enabling shorter intervals between two excitation pulses.

The three radicals $R^1$, $R^2$, and $R^3$ may be identical or different. If $R^2$ and $R^3$ are identical to $R^1$, no additional signals appear in the spectrum. If $R^2$ and $R^3$ are different from $R^1$, they are selected from H, $CH_3$, and $CH_2CH_3$, so that only a few additional signals are generated in $^1$H and $^{13}$C NMR spectra. In that case $R^2$ and $R^3$ are preferably H or $CH_3$.

Of the compounds of the formulae (1) and (2), those of the formula (1) are preferred.

The compound of the formulae (1) or (2) preferably has one or two hydrogen atoms bonded to the benzene ring.

In the case of one preferred embodiment of the invention, two hydrogen atoms are bonded on the benzene ring. Through a suitable arrangement of the two hydrogen atoms and of the further substituents on the ring, it becomes possible for the two hydrogen atoms to have different spin-lattice relaxation times. The two hydrogen atoms are preferably not adjacent, in order to prevent splitting of their signals in the $^1$H NMR spectrum. With particular preference the two hydrogen atoms are meta to one another.

In the compounds of the formulae (1) and (2), furthermore, there is preferably at least one hydrogen atom arranged on the benzene ring ortho to at least one $CF_3$ substituent or $CH_3$ substituent. As a result of the $CF_3$ OR $CH_3$ group adjacent to the aromatic hydrogen atom, there is a dipole-dipole interaction, causing a marked reduction in the spin-lattice relaxation time of the hydrogen atom. In the case of the compound tetrachloronitrobenzene, for instance, the spin-lattice relaxation time $T_1$ of the aromatic hydrogen atom is more than 10 s. If one of the chlorine atoms adjacent to the hydrogen atom is replaced by a $CF_3$ group, then $T_1$ reduces to about 5 s. This correlates with a significant time saving when a large number of FIDs are to be summated. If two of the abovementioned substituents are arranged in ortho-position to the aromatic hydrogen atom, then the spin-lattice relaxation time of the hydrogen atom may be reduced further still, and values of down to 2 s or less can be achieved.

Of the two stated groups —$CH_3$ and —$CF_3$, the $CF_3$ group is preferred, since it does not generate any additional signals in a $^1$H or $^{13}$C NMR spectrum.

The compounds of the formula (1) and (2) according to the invention preferably contain at least one hydrogen atom whose relaxation time is not more than 5 s and whose signal in a $^1$H NMR spectrum appears at a chemical shift of at least 8 ppm.

A preferred embodiment is also represented by compounds of the formulae (1) and (2) in which two hydrogen atoms bonded on the benzene nucleus are arranged ortho to at least one $CF_3$ substituent or $CH_3$ substituent. In the case of these compounds, one of the two hydrogen atoms is preferably ortho to two of the stated substituents, to give a compound both of whose aromatic hydrogen atoms exhibit low spin-lattice relaxation times of preferably less than or equal to 5 s, with one of the two hydrogen atoms having an even lower spin-lattice relaxation time of preferably 2 s or less. When such a compound is used as a standard in quantitative NMR spectroscopy, a system suitability test is available accordingly, and indicates whether the integrals of the measured signals have been correctly captured. This system suitability test will be elucidated in more detail later on.

In a further preferred embodiment, the compounds of the formulae (1) and (2) have two or more hydrogen atoms on the benzene nucleus, and at least two of these hydrogen atoms are ortho to at least one substituent, selected from —$NO_2$ and —$C(=O)OR_6$. As a result, in the $^1H$ NMR spectrum, the signals of the two hydrogen atoms ortho to the electron-withdrawing groups appear at high chemical shifts, preferably at δ≥8, and hence the probability of overlap with signals of the analyte is low. These two hydrogen atoms are preferably not adjacent, meaning that they are meta or para, preferably meta, to one another, and so two singlets are obtained in the $^1H$ NMR spectrum.

If, furthermore, one of the two aromatic hydrogen atoms is ortho to a $CF_3$ group or $CH_3$ group, its spin-lattice relaxation time $T_1$ is reduced significantly relative to that of the other hydrogen atom on the benzene ring. In this case the spin-lattice relaxation times $T_1$ of the two hydrogen atoms differ by preferably at least 3 s, more preferably by at least 5 s, and very preferably by at least 7 s. As already mentioned above, the chemical shift of these two hydrogen atoms on the benzene ring in a $^1H$ NMR spectrum is preferably at least 8 ppm.

If the quantitative NMR spectroscopy is carried out using the integrals of signals whose nuclei exhibit significantly different spin-lattice relaxation times $T_1$, then false results are obtained unless a sufficient time is awaited between two excitation pulses, so that predominantly all of the nuclei have relaxed again. If the compound described above is used as a standard in quantitative NMR spectroscopy, then two singlets appear with high chemical shift in the $^1H$ NMR spectrum, these singlets originating from the two aromatic hydrogen atoms not arranged adjacent to one another. If the waiting time between two successive excitation pulses were to be too low, so that the hydrogen atom with the longer spin-lattice relaxation time is not sufficiently relaxed, these two signals would have different intensities (integrals). In the case of identical intensities of the two singlets, therefore, it can be assumed that the measurement has not been falsified by inadequate waiting times between two excitation pulses.

A standard of this kind therefore allows high reliability in the quantitative NMR spectroscopy of compounds whose nuclei exhibit strongly different spin-lattice relaxation times $T_1$. If the two aromatic hydrogen atoms in the standard of the invention have spin-lattice relaxation times of 4 s and 10 s, for example, and if their signals in the spectrum have the same intensities, then it is ensured that all of the nuclei in the analyte as well that have spin-lattice relaxation times of up to 10 s have been correctly detected quantitatively. If compounds of this kind are used as a standard in NMR spectroscopy, therefore, a system suitability test (system self-test) is integrated and indicates whether a correct detection of the signal intensities took place for the waiting times used between two successive excitation pulses.

In one preferred embodiment of the compounds of the formulae (1) and (2), the benzene ring carries only one hydrogen atom. This minimizes the number of possible signals by the standard $^1H$ NMR spectrum, reducing the number of possible overlaps with signals of the analyte. This one hydrogen atom on the benzene ring is preferably ortho to at least one $CF_3$ substituent or $CH_3$ substituent, more preferably ortho to at least one $CF_3$ substituent, so that the spin-lattice relaxation time of the hydrogen atom is reduced, preferably to 5 s or less.

Also embraced by the present invention is any NMR standard which comprises one of the abovementioned compounds of the invention. This standard may be a solid or a solution in a suitable solvent. The standard of the invention may be used both for qualitative and for quantitative NMR measurements. The NMR standard of the invention may be used both as an internal and as an external standard.

Furthermore, the present invention also embraces the use of one or more of the abovementioned compounds of the invention as standards in $^1H$, $^{13}C$, $^{15}N$, $^{19}F$, or $^{31}P$ nuclear magnetic resonance spectroscopy. Particularly preferred is their use in quantitative NMR spectroscopy.

The use according to the invention as an internal standard in NMR spectroscopy comprises the addition of one of the compounds of the invention to the solution under analysis, containing the compound under analysis (the analyte), the dissolving of the added compound in the solution under analysis, and the measurement of the solution under analysis, admixed with the standard, in an NMR spectrometer.

Additionally embraced by the present invention is a nuclear magnetic resonance spectroscopy method in which the nuclear spin resonance of one of the atoms $^1H$, $^{13}C$, $^{15}N$, $^{19}F$, or $^{31}P$ is detected, and in which the standard used comprises one or more of the abovementioned compounds of the invention. More preferably the NMR method is a quantitative NMR method.

Lastly, the present invention also embraces a method for determining an analyte by means of $^1H$, $^{13}C$, $^{15}N$, $^{19}F$, or $^{31}P$ nuclear magnetic resonance spectroscopy, in which the standard used comprises one or more of the abovementioned compounds of the invention. The determination by means of the method of the invention may be a qualitative and/or quantitative determination.

Shown below are particularly preferred compounds according to the present invention.

Compounds of the formula (3):

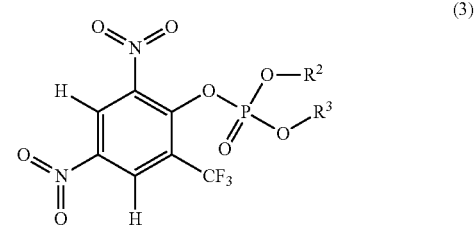

(3)

where the radicals $R^2$ and $R^3$ independently of one another are selected from the phenyl radical shown in the formula (3), H, $CH_3$, and $CH_2$—$CH_3$, preferably from the phenyl radical, H, and $CH_3$.

Preferred representatives of the compounds of the formula (3) are the compounds of the following formulae:

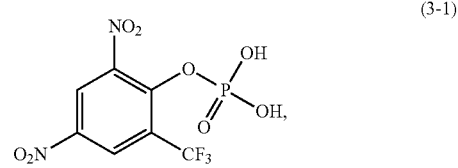

(3-1)

-continued

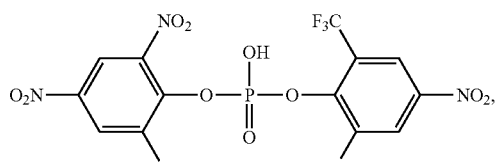
(3-2)

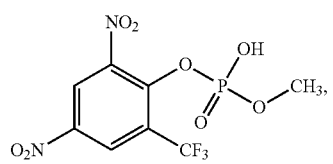
(3-3)

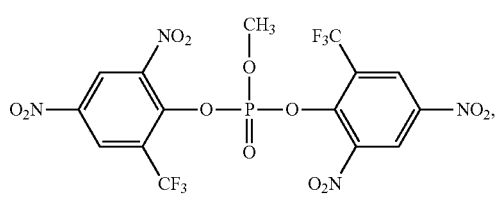
(3-4)

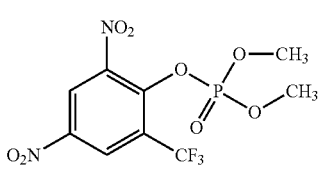
(3-5)

and

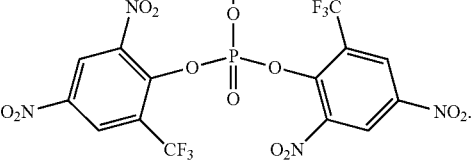
(3-6)

In the compounds of the formula (3), both aromatic hydrogen atoms exhibit a high chemical shift, with the hydrogen atom between the two $NO_2$ groups being shifted even further in the downfield direction. In a $^1H$ NMR spectrum, accordingly, two singlets are obtained. Furthermore, the hydrogen atom adjacent to the $CF_3$ group shows a spin-lattice relaxation time $T_1$ of less than 5 s, while that between the two $NO_2$ groups shows a relatively high spin-lattice relaxation time of more than about 10 s. When a compound of the formula (3) is used as a standard in quantitative NMR spectroscopy, therefore, a system suitability test (system self-test) is possible, since in the case of identical signals (integrals) of the two singlets of the hydrogen atom on the benzene ring, it is ensured that all nuclei with spin-lattice relaxation times of up to 10 s in the solution under analysis have been correctly detected.

Moreover, these compounds can be used as a standard in $^1H$, $^{13}C$, $^{15}N$, $^{19}F$, and $^{31}P$ nuclear magnetic resonance spectroscopy.

Compounds of the formula (4):

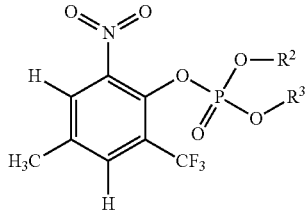
(4)

where the radicals $R^2$ and $R^3$ independently of one another are selected from the phenyl radical shown in the formula (4), H, $CH_3$, and $CH_2$—$CH_3$, preferably from the phenyl radical, H, and $CH_3$.

Preferred representatives of the compounds of the formula (4) are the compounds of the following formulae:

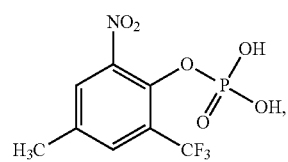
(4-1)

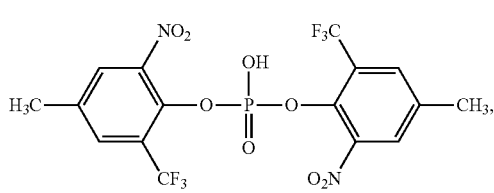
(4-2)

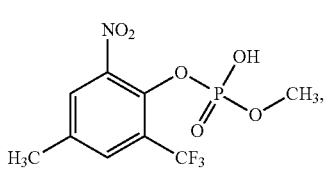
(4-3)

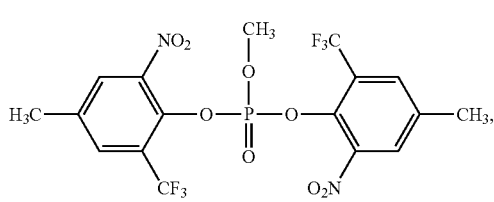
(4-4)

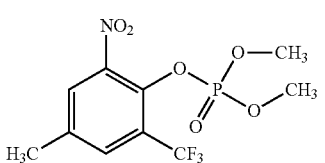
(4-5)

and (4-6)

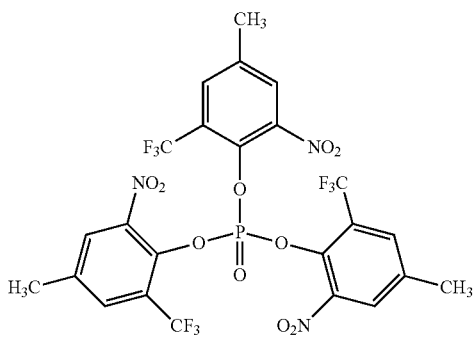

In the compounds of the formula (4), the aromatic hydrogen atom between the $NO_2$ group and the $CH_3$ group shows a spin-lattice relaxation time of less than about 5 s, while the aromatic hydrogen atom between the $CH_3$ group and the $CF_3$ group, owing to the dipole-dipole interactions with both groups, shows an even lower spin-lattice relaxation time of about 2 s. Using these compounds as a standard in quantitative NMR spectroscopy, proper detection of all nuclei in the solution under analysis is ensured that exhibit spin-lattice relaxation times of 2 to 5 s.

Furthermore, the $CF_3$ group adjacent to the phosphoric acid group reduces the spin-lattice relaxation time of the phosphorus nucleus.

Moreover, these compounds can be used as a standard in $^1H$, $^{13}C$, $^{15}N$, $^{19}F$, and $^{31}P$ nuclear magnetic resonance spectroscopy.

Compounds of the formula (5):

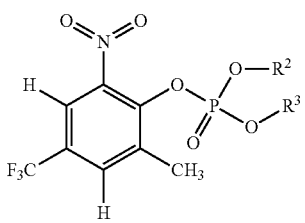

(5)

where the radicals $R^2$ and $R^3$ independently of one another are selected from the phenyl radical shown in the formula (5), H, $CH_3$, and $CH_2$—$CH_3$, preferably from the phenyl radical, H, and $CH_3$.

Preferred representatives of the compounds of the formula (5) are the compounds of the following formulae:

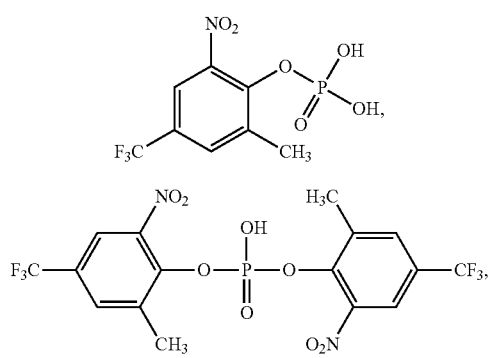

(5-1)

(5-2)

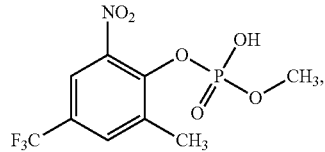

(5-3)

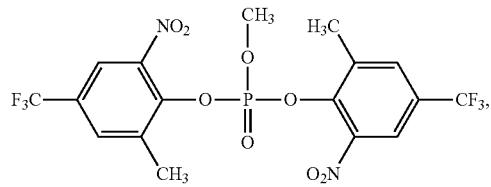

(5-4)

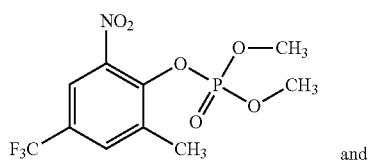

(5-5)

and

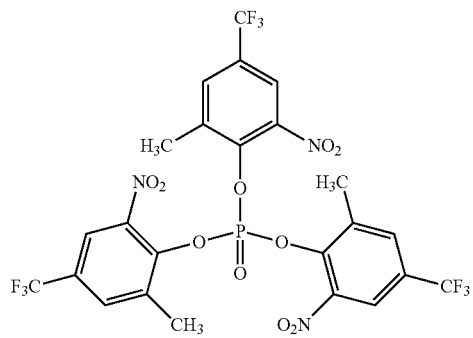

(5-6)

The properties of the compounds of the formula (5) are comparable with those of the formula (4).

Compounds of the formula (6):

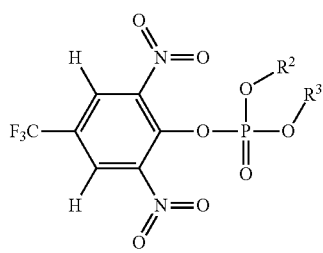

(6)

where the radicals $R^2$ and $R^3$ independently of one another are selected from the phenyl radical shown in the formula (6), H, $CH_3$, and $CH_2$—$CH_3$, preferably from the phenyl radical, H, and $CH_3$.

Preferred representatives of the compounds of the formula (6) are the compounds of the following formulae:

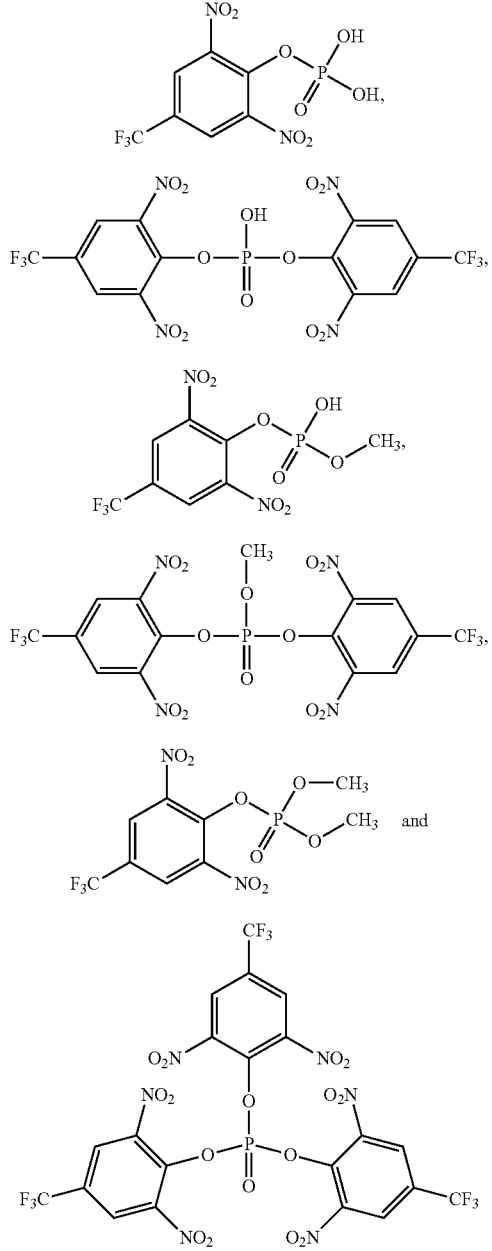

In the compounds of the formula (6), the two hydrogen atoms on the benzene nucleus exhibit a high chemical shift, since they are adjacent (ortho) to an $NO_2$ group in each case. Moreover, they are adjacent to a $CF_3$ group, thereby reducing their spin-lattice relaxation time. Since the substituted phenyl radical is symmetrical in relation to the arrangement of the substituents, it generates only one singlet in a $^1H$ NMR spectrum. If $R^2$ and $R^3$ are the same substituted phenyl radical, the resulting compound, when used as a standard in NMR spectroscopy, will show only one singlet in a $^1H$ NMR spectrum.

Moreover, these compounds can be used as a standard in $^1H$, $^{13}C$, $^{15}N$, $^{19}F$, and $^{31}P$ nuclear magnetic resonance spectroscopy.

Compounds of the formula (7):

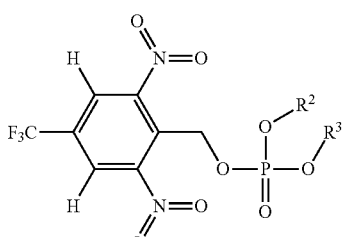

where the radicals $R^2$ and $R^3$ independently of one another are selected from the benzyl radical shown in the formula (7), H, $CH_3$, and $CH_2$—$CH_3$, preferably from the benzyl radical, H, and $CH_3$.

Preferred representatives of the compounds of the formula (7) are the compounds of the following formulae:

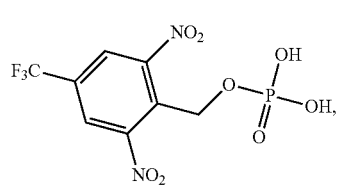

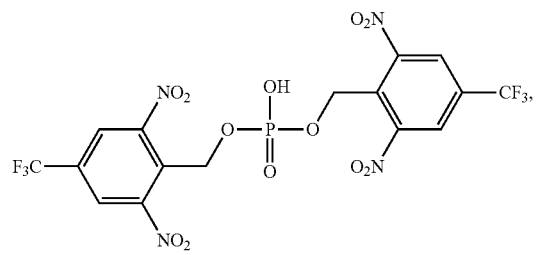

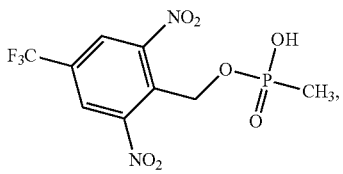

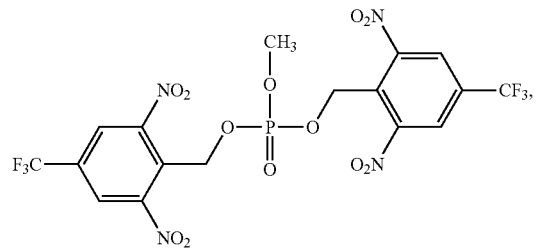

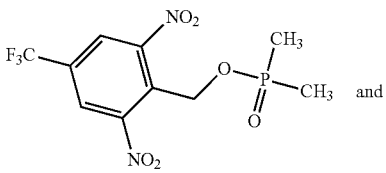

(7-6)

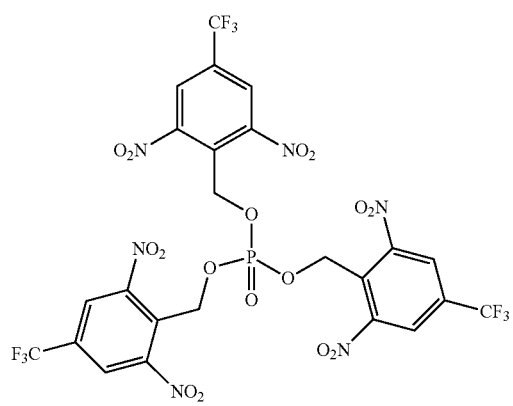

The compounds of the formula (7) have similar properties to those of the formula (6), with, in addition, the spin-lattice relaxation time of the phosphorus atom being reduced as a result of the CH$_2$ group of the benzyl radical.

Compounds of the formula (8):

(8)

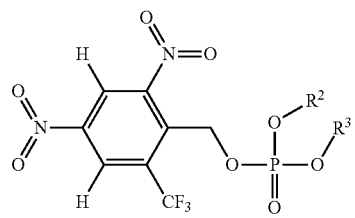

where the radicals R$^2$ and R$^3$ independently of one another are selected from the benzyl radical shown in the formula (8), H, CH$_3$, and CH$_2$—CH$_3$, preferably from the benzyl radical, H, and CH$_3$.

Preferred representatives of the compounds of the formula (8) are the compounds of the following formulae:

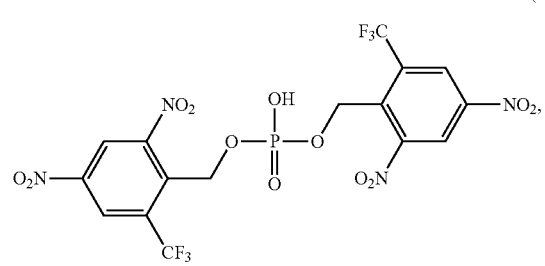

(8-1)

(8-2)

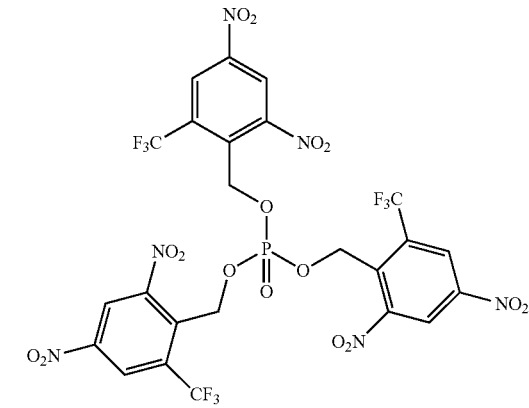

(8-3)

(8-4)

(8-5)

and (8-6)

In contradistinction to the compounds of the formula (7), the compounds of the formula (8) show two singlets, with a high shift, in a $^1$H NMR spectrum, since the benzene ring is not symmetrically substituted. Moreover, the two aromatic hydrogen atoms have similarly different spin-lattice relaxation times as described above for the compounds of the formula (3). They can therefore provide a system suitability test as described above, when used as a standard in quantitative NMR spectroscopy.

The compounds of the invention may be prepared, for example, by the reaction of the corresponding phenol compounds or benzyl alcohol compounds with phosphoric acid (H$_3$PO$_4$) or phosphonic acid (H$_3$PO$_3$), respectively, or with a more reactive derivative of the corresponding acid, such as phosphorus oxytrichloride P(═O)Cl$_3$, for example. Other known processes for preparing organic phosphoric esters or phosphonic esters may also be used. Shown below, schematically, is the reaction equation for the preparation of the compound of the formula (3-6):

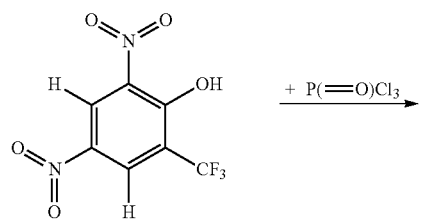 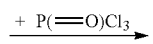

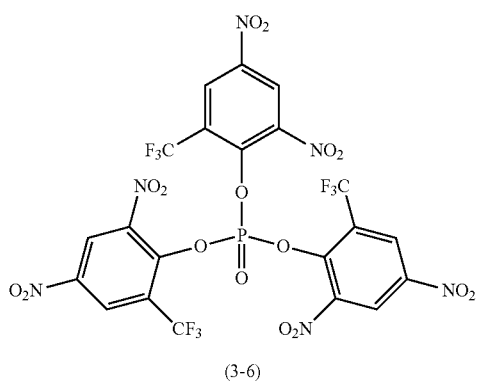

(3-6)

In addition to the compounds specified above, the compound of the formula (9) below may also be used as a preferred standard in NMR spectroscopy, preferably in quantitative NMR spectroscopy:

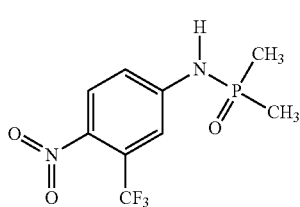

(9)

This compound, as well as carbon atoms and hydrogen atoms, also contains the atoms N, P, and F, and can therefore be used as a standard in $^1$H, $^{13}$C, $^{15}$N, $^{19}$F, and $^{31}$P nuclear magnetic resonance spectroscopy. The $^1$H NMR spectrum of this compound will show, downfield, three different signals of the three aromatic hydrogen atoms, these atoms also having different spin-lattice relaxation times $T_1$. This preferred compound can therefore also be employed as a standard in quantitative NMR spectroscopy, permitting the system suitability test described above.

$R^6$

In the reference examples below, $^1$H NMR spectra of the following compounds were measured:

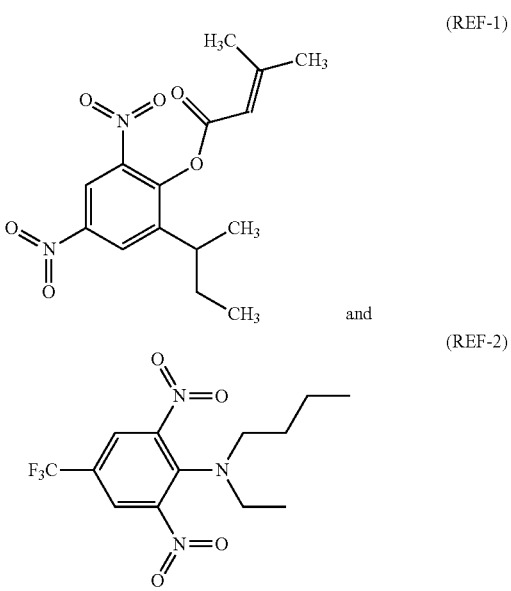

These two compounds are not encompassed by the present invention, but show very clearly the effects of the specific arrangement of the $NO_2$ and $CF_3$ substituents on the benzene ring.

FIG. 1 shows the $^1$H NMR spectrum of the reference compound (REF-1). The two aromatic hydrogen atoms are adjacent to one or two $NO_2$ substituents, and so their signals appear well above a chemical shift of 8. The hydrogen atom with one adjacent $NO_2$ substituent appears at $\delta=8.5$, while the hydrogen atom with two adjacent $NO_2$ substituents is shifted even further downfield, and appears at $\delta=8.7$. Furthermore, in the spectrum shown in FIG. 1, the relaxation times $T_1$ of the various hydrogen atoms in the compound are also listed. The hydrogen atom with the highest chemical shift ($\delta=8.7$), which is unable to enter into dipole-dipole interaction with adjacent substituents, has a relatively high relaxation time $T_1$ of approximately 7.3 s. In contrast, the hydrogen atom with the chemical shift of 8.5 exhibits a much lower relaxation time $T_1$ of approximately 1.8 s, since here there is a dipole-dipole interaction with the adjacent alkyl substituent.

The two aromatic hydrogen atoms of the compound of the formula (REF-1) have significantly different spin-lattice relaxation times $T_1$, and so this compound is suitable for demonstrating the system suitability test described above. Table 1 shows the relative integrals of the two aromatic hydrogen atoms as a function of the relaxation delay D1.

TABLE 1

| Acquisition time AQ [s] | Relaxation delay D1 [s] | Sum of AQ and D1 [s] | Integral of the signal at $\delta = 8.7$ ppm | Integral of the signal at $\delta = 8.5$ ppm |
| --- | --- | --- | --- | --- |
| 1.328 | 1 | 2.3 | 79.1 | 100.0 |
| 2.656 | 1 | 3.7 | 84.9 | 100.0 |
| 2.656 | 2 | 4.7 | 87.4 | 100.0 |
| 2.656 | 5 | 7.7 | 92.5 | 100.0 |
| 2.656 | 10 | 12.7 | 97.5 | 100.0 |
| 2.656 | 20 | 22.7 | 99.0 | 100.0 |
| 2.656 | 30 | 32.7 | 100.0 | 100.0 |
| 2.656 | 60 | 62.7 | 100.0 | 100.0 |

It is clearly seen that up to a relaxation delay of 20 s, different integrals are obtained for the two aromatic hydrogen atoms, and errors could therefore occur in the case of quantitative determinations by means of NMR spectroscopy. In the case of spectra recorded with a relaxation delay of 30 s or longer, it will be seen at a glance, from the matching integrals of the two aromatic hydrogen atoms, that all hydrogen atoms with a spin-lattice relaxation time of up to 7.3 were correctly detected.

Figure 2:
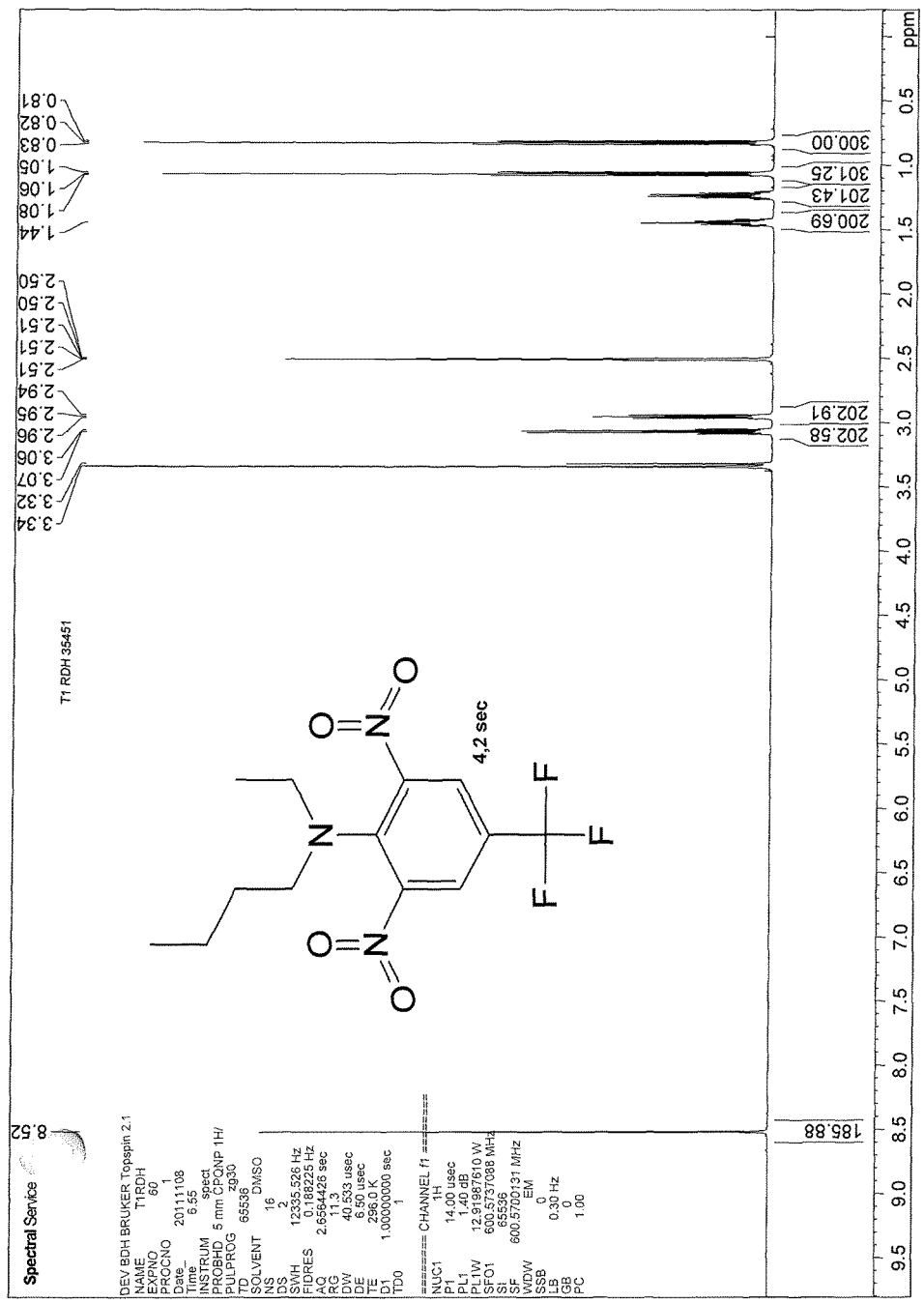

FIG. 2 shows the $^1$H NMR spectrum of the compound (REF-2), i.e., of benfluralin. Since the benzene ring is symmetrically substituted, the signals of the two aromatic hydrogen atoms appear at the same chemical shift δ=8.5. The $CF_3$ substituent enables a dipole-dipole interaction with the two hydrogen atoms, and so their spin-lattice relaxation time $T_1$ is approximately 4.2 s.

The invention claimed is:

1. A method of identifying an analyte wherein the method comprises:
   providing a standard compound for nuclear magnetic resonance spectroscopy, the standard compound comprised of the formula (1) or (2)

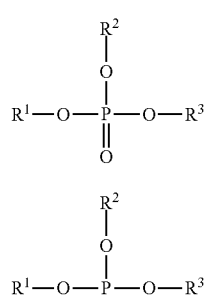

where $R^1$ is a phenyl radical or benzyl radical whose benzene ring has the following substituents:
   at least one —$CF_3$ substituent,
   at least one nitrogen-containing substituent selected from —$NO_2$ and —$NR^4R^5$, where $R^4$ and $R^5$ independently of one another are selected from H, $CH_3$, and $CH_2CH_3$, optionally one or two substituents selected from Cl, Br, I, —$CH_3$, and —C(=O)$OR^6$, where $R^6$ is selected from H, $CH_3$, and $CH_2CH_3$, and
   at least one hydrogen atom, where at least one of the hydrogen atoms is ortho to at least one substituent selected from —$NO_2$ and —C(=O)$OR^6$, and
   where $R^2$ and $R^3$ are the same as $R^1$ or independently of one another are selected from H, $CH_3$, and $CH_2CH_3$;
   detecting the nuclear magnetic resonance of one of the atoms $^1$H, $^{13}$C, $^{15}$N, $^{19}$F, or $^{31}$P; and
   determining the analyte quantitatively.

2. The method according to 1, wherein the benzene ring carries precisely two hydrogen atoms as substituents.

3. The method according to claim 2, wherein the two hydrogen atoms are meta to one another on the benzene ring.

4. The method according to claim 1, wherein at least one hydrogen atom on the benzene ring is ortho to at least one $CF_3$ substituent or $CH_3$ substituent.

5. The method according to claim 1, wherein at least two hydrogen atoms on the benzene ring are ortho to at least one $CF_3$ substituent or $CH_3$ substituent.

6. The method according to claim 1, wherein at least two hydrogen atoms on the benzene ring are ortho to at least one substituent selected from —$NO_2$ and —C(=O)$OR^6$.

7. The method as claimed in claim 1, wherein the benzene ring carries only one hydrogen atom as substituent, and the hydrogen atom on the benzene ring is preferably ortho to at least one $CF_3$ substituent or $CH_3$ substituent.

8. The method according to claim 1, wherein, in a $^1$H nuclear magnetic resonance spectroscopy, with the chemical shift of tetramethylsilane set as 0 ppm, the chemical shift δ of at least one hydrogen atom on the benzene ring is at least 8 ppm.

9. The method as claimed in claim 8, wherein the spin-lattice relaxation time $T_1$ of the at least one hydrogen atom having the chemical shift of at least 8 ppm is not more than 5 s.

10. The method according to claim 8, wherein the chemical shift of two hydrogen atoms on the benzene ring is at least 8 ppm, and the relaxation times of the two hydrogen atoms differ by at least 3 s.

11. The method according to claim 1, wherein the compound is selected from the compounds having the formulae (3) to (8):

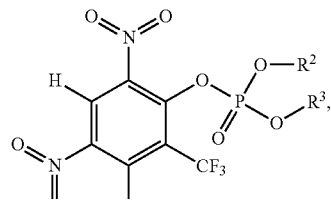

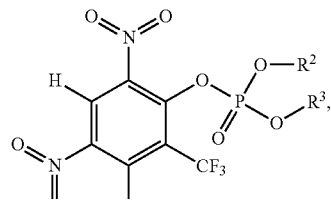

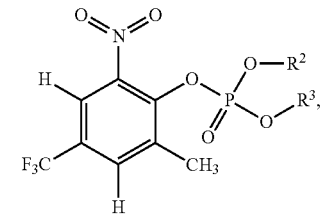

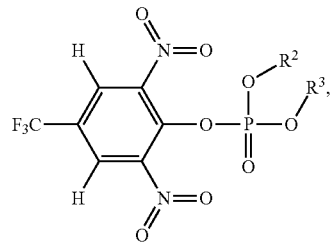

-continued
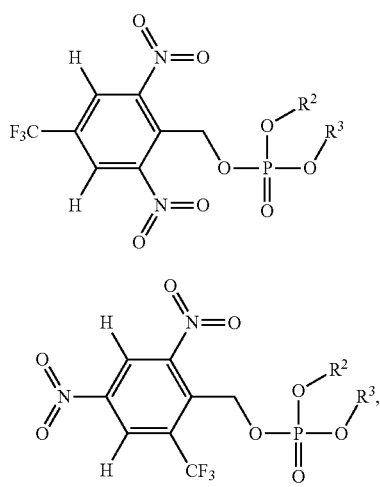
(7)
(8)
where the radicals R² and R³ independently of one another are selected from the phenyl radical or benzyl radical shown in the respective formulae, H, CH₃, and CH₂—CH₃, preferably from the phenyl radical or benzyl radical, H, and CH₃.
12. The method according to claim 11, wherein the compound is selected from the following compounds:
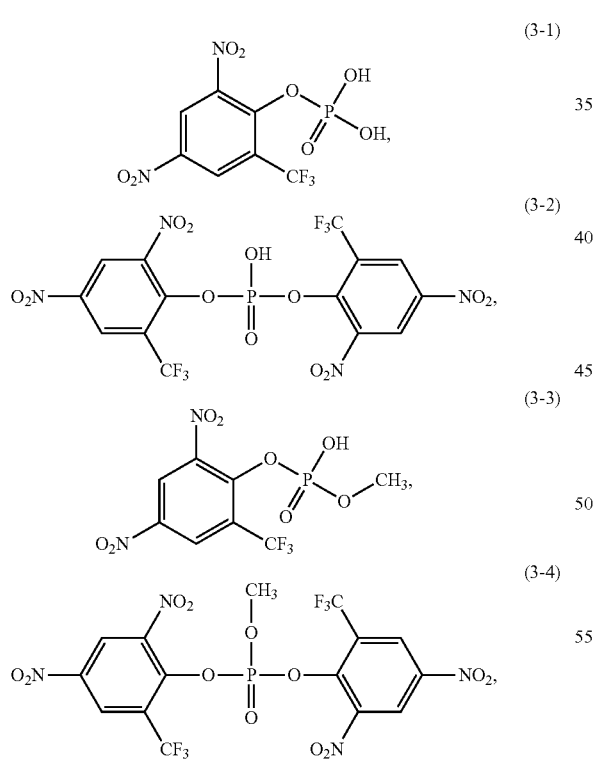
(3-1)
(3-2)
(3-3)
(3-4)
(3-5)
-continued
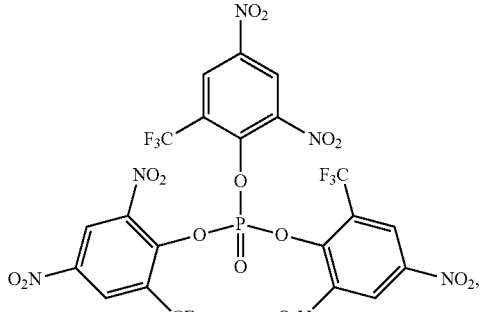
(3-6)
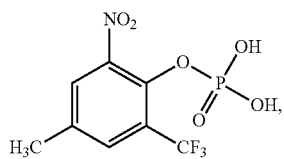
(4-1)
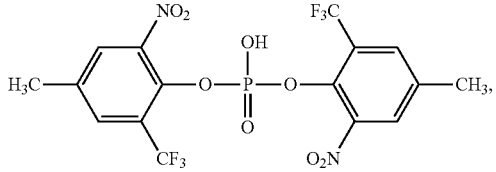
(4-2)
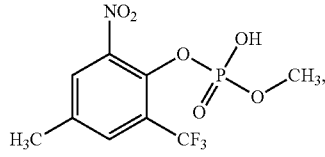
(4-3)
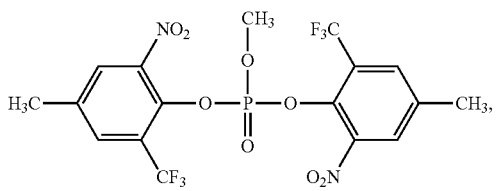
(4-4)
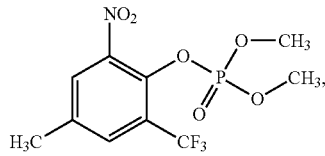
(4-5)
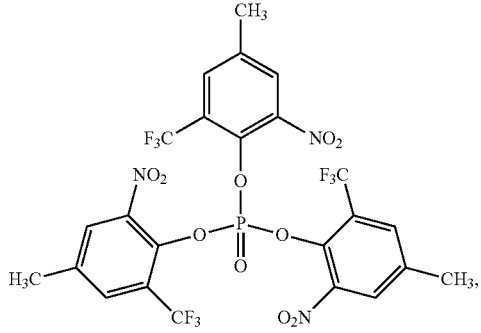
(4-6)

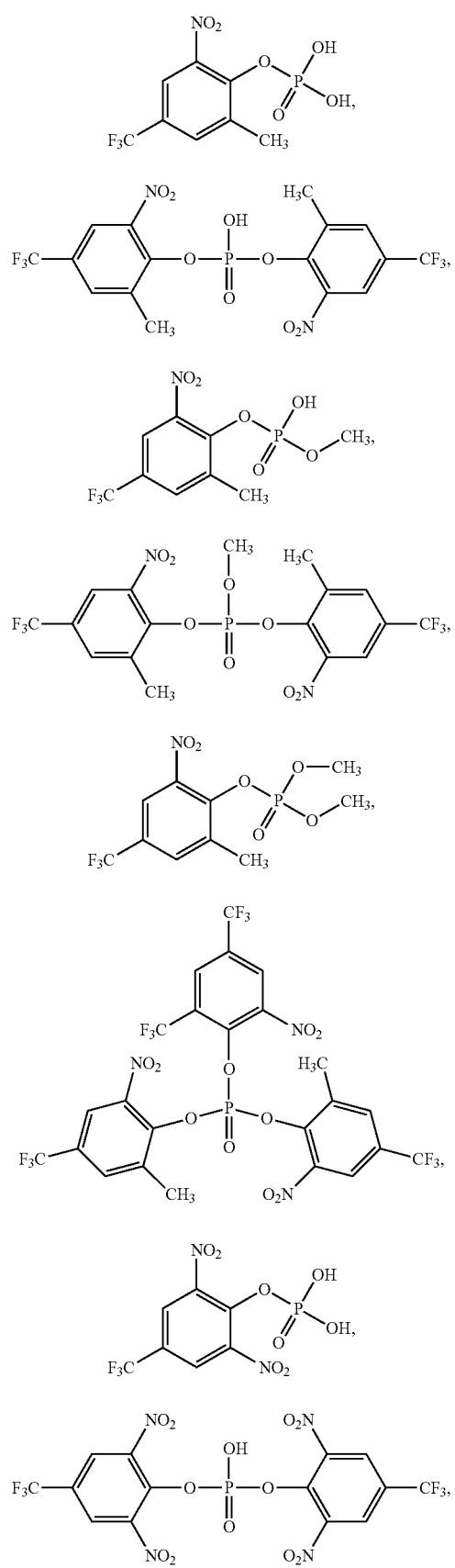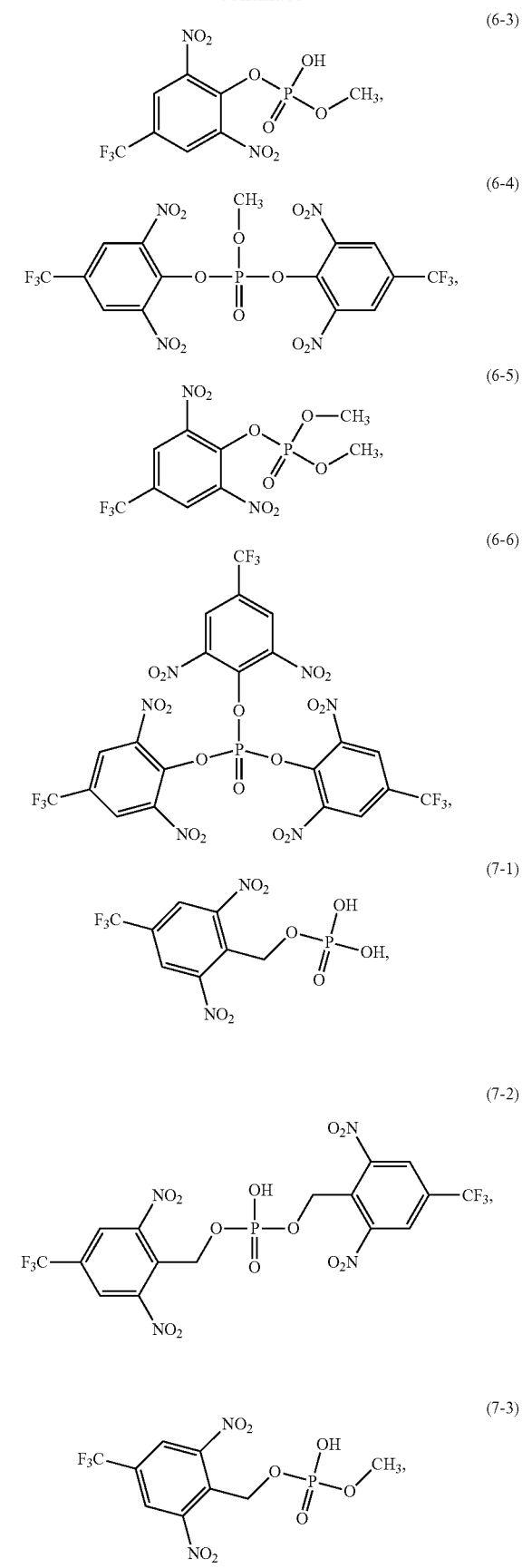

(7-4)
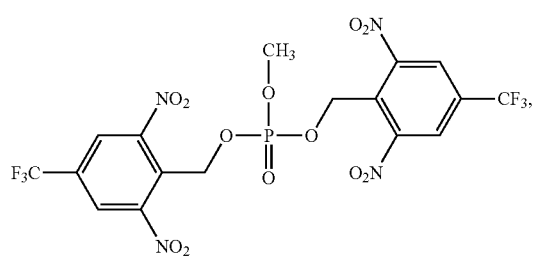
(7-5)
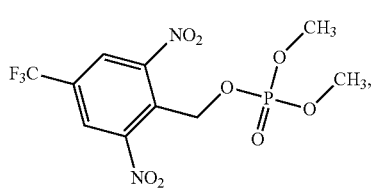
(7-6)
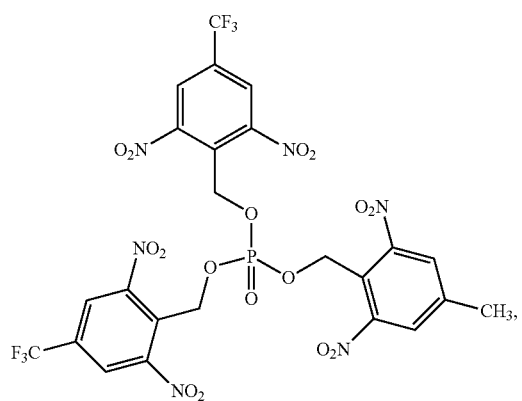
(8-1)
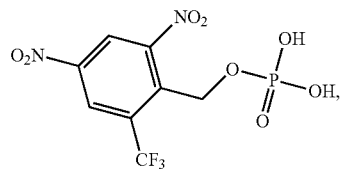
(8-2)
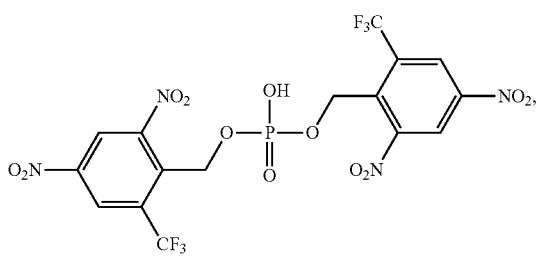
(8-3)
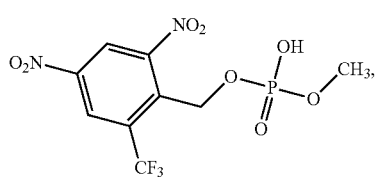
(8-4)
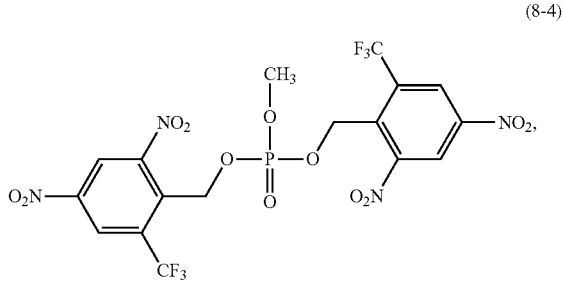
(8-5)
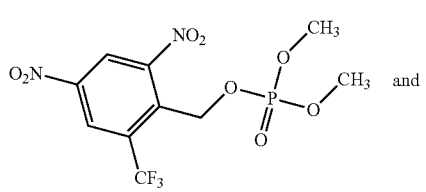
and
(8-6)
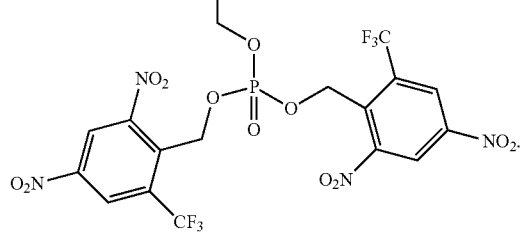
13. A method of identifying an analyte wherein the method comprises:
providing a standard compound for nuclear magnetic resonance spectroscopy, the standard compound comprised of the formula (9)
(9)
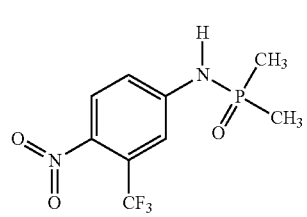
detecting the nuclear magnetic resonance of one of the atoms $^1H$, $^{13}C$, $^{15}N$, $^{19}F$, or $^{31}P$; and
determining the analyte quantitatively.
* * * * *